United States Patent [19]

Neumann et al.

[11] 4,018,968
[45] Apr. 19, 1977

[54] COATED MAGNETIC RECORDING MEDIA

[75] Inventors: Ute Neumann, Frankenthal; Hermann Roller, Ludwigshafen; Job-Werner Hartmann, Ludwigshafen; Joachim Hack, Ludwigshafen; Herbert Motz, Ludwigshafen; Werner Ostertag, Willstaett, all of Germany

[73] Assignee: BASF Aktiengesellschaft, Ludwigshafen, Germany

[22] Filed: Sept. 19, 1974

[21] Appl. No.: 507,457

[30] Foreign Application Priority Data

Oct. 5, 1973 Germany ............................ 2350063

[52] U.S. Cl. ............................ 428/539; 252/62.54; 428/900
[51] Int. Cl.$^2$ .......................................... H01F 10/02
[58] Field of Search ............................ 117/235–240; 252/62.54; 427/127–132, 47, 48; 428/900, 539

[56] References Cited

UNITED STATES PATENTS

| | | | |
|---|---|---|---|
| 3,692,884 | 9/1972 | Gaskell | 117/235 X |
| 3,704,152 | 11/1972 | Hartmann | 117/237 X |
| 3,719,525 | 3/1973 | Patel et al. | 117/237 |
| 3,778,308 | 12/1973 | Roller et al. | 117/237 X |
| 3,793,074 | 2/1974 | Frankenthal et al. | 117/235 |

*Primary Examiner*—Bernard D. Pianalto
*Attorney, Agent, or Firm*—Johnston, Keil, Thompson & Shurtleff

[57] ABSTRACT

Coated magnetic recording media, especially video tapes and computer tapes, comprising a non-magnetic base carrying a magnetic coating which consists of a dispersion, essentially containing a finely divided magnetic pigment in an organic binder and at least one lubricant. A compound of the formula

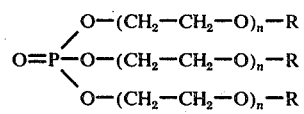

in which $n$ is an integer of from 1 to 3 and R is alkyl, alkoxyalkyl or aralkyl, each of 3 to 18 carbon atoms, is used as a lubricant. The products have high abrasion resistance coupled with only little transfer of material to the magnetic heads even under fluctuating climatic conditions.

5 Claims, No Drawings

COATED MAGNETIC RECORDING MEDIA

This application discloses and claims subject matter described in German patent application No. P 23,50,063.2, filed Oct. 5, 1973, which is incorporated herein by reference.

The invention is concerned with coated magnetic recording media and in particular with video tapes and computer tapes which have advantageous self-lubricating properties.

Magnetic tapes for use as video tapes and computer tapes must have high abrasion resistance coupled with excellent frequency characteristics and high recording and playback sensitivity. For example, in television recording equipment, the relative velocity between the magnetic head and the magnetic tape in contact with it is in excess of 20 m/sec. When using a computer tape, the magnetic tape is particularly subjected to wear as a result of the frequent changes in direction of travel in the tapes before the head. The abrasion resistance and life of the magnetic coatings of such tapes are therefore of particular importance.

It is known that coated magnetic recording media of improved abrasion resistance can be manufactured by adding solid or liquid lubricants, such as graphite, molybdenum disulfide, stearic acid, oleic acid, fatty acid esters, petroleum jelly or mineral oil to the magnetic coating. German Printed Application No. 1,005,754 and U.S. Pat. No. 3,003,965 have disclosed the addition of acid phosphorus compounds and German Published Application No. 1,669,602 has disclosed the addition of a divalent or trivalent salt of an oxy-acid derived from phosphorus and having organic groups of at least 8 carbon atoms. A disadvantage of the use of acid phosphorus compounds is that they impair somewhat the magnetic properties of the tapes containing gamma-iron-(III) oxide. The other conventional lubricant additives also do not provide the properties required for industrial application.

Essential factors in high sensitivity and good characteristics for recording high data densities are the choice of the magnetic pigment, the packing density of the magnetic material in the magnetic coating, as smooth a surface of the magnetic coating as possible, and a tape which is as flexible and supple as possible under all climatic conditions. It is the object of the present invention to provide a magnetic tape improved in this respect, which substantially has the required properties, exhibits uniform internal lubrication of the magnetic coating whilst at the same time the magnetic tapes remain plane under all climatic conditions, and is particularly suitable for use as a magnetic recording medium of long life, high sensitivity and good frequency response for video and computer recordings.

We have found that magnetic recording media comprising a base carrying a magnetic coating, which essentially consists of a dispersion of a finely divided magnetic pigment and at least one lubricant in a binder, substantially exhibit the desired properties if the lubricant they contain is a compound of the formula (I)

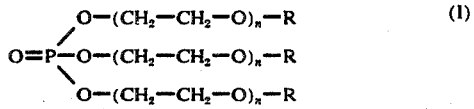

wherein $n$ is an integer of from 1 to 3 and R is alkyl, alkoxyalkyl or aralkyl, each of 3 to 18 carbon atoms.

The lubricants of the formula (I) present in the magnetic coatings of the coated magnetic recording media according to the invention are liquids with viscosities of from 10 to 500 centipoise and preferably of from 20 to 500 centipoise. Amongst them, the trialkoxyethyl esters of phosphoric acid have proved advantageous, the tri-n-butoxyethyl ester of phosphoric acid, of the formula (II)

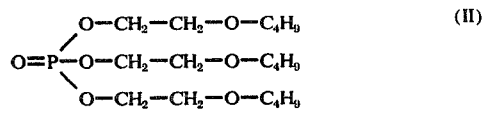

having proved very particularly advantageous.

The magnetic coating preferably contains from 0.1 to 20 parts by weight of lubricant per 100 parts by weight of the magnetic pigment used, and the optimum amount, which is principally co-determined by the nature of the binder and of the lubricant, can readily be established by some preliminary tests. Of course it is possible, and in some cases advantageous, to use mixtures of the lubricants of the formula (I) with other conventional slip agents or lubricants, such as alkyl esters of fatty acids or aliphatic dicarboxylic acids, wherein the esters preferably are of at least 16 carbon atoms, or polysiloxanes. It is surprising that a distinct improvement in the resulting magnetic recording media is achieved with such mixtures even if only about 20 percent by weight of the total lubricant consists of compounds of the formula (I). In general, the content of compounds of the formula (I) is from about 20 to 100 percent by weight of the total amount of lubricants employed.

The conventional organic, mostly polymeric, binders such as vinyl chloride polymers, acrylate polymers, polyvinyl acetals, such as polyvinyl formal or polyvinyl butyral, high molecular weight epoxide resins, polyesters, polycarbonates, polyurethanes and mixtures of these and similar binders can be used as binders for the magnetic recording media according to the invention. Polyester-polyurethanes and polyether-polyurethanes which are soluble in volatile organic solvents have proved very suitable, either when used as sole binders or when used in admixture with minor amounts of other binders such as, in particular, from 10 to 50% by weight, based on the total amount of binder, of epoxide resin binders, such as bisphenol A-epichlorohydrin condensates, or vinyl chloride copolymers; above all, polyurethanes which are obtained from a linear aliphatic polyester or polyether and a polyisocyanate, are elastomeric and practically free from isocyanate groups, and are in some cases commercially available have proved suitable (compare Saunders-Frisch, Polyurethanes, Chemistry and Technology, Part II, Chapter IX, New York 1964 and the literature quoted there, and also U.S. Pat. No. 2,899,411 and German Printed Application No. 1,106,959). Elastomeric linear polyester-urethanes which can be obtained by reaction of hydroxyl-containing linear polyesters, obtained from an aliphatic diol of 2 to 6 carbon atoms and an aliphatic dicarboxylic acid of 2 to 12 carbon atoms and optionally an aliphatic hydroxycarboxylic acid or its lactone of 3 to 12 carbon atoms and a diisocyanate, under conditions such that all isocyanate groups can react with a hydroxyl group, have proved particularly suitable.

Amongst the above, the elastic, thermoplastic reaction products of hydroxyl-containing thermoplastic polyesters of adipic acid and 1,4-butanediol and/or ethylene glycol with diisocyanates, such as, in particular, 4,4'-diisocyanato-diphenylmethane, 4,4'-diisocyanatodiphenylpropane-(2,2), 4,4'-diisocyanato-dicyclohexylmethane, 4,4'-diisocyanato-dicyclohexylpropane-(2,2), 1,5-naphthylenediisocyanate or toluylene-diisocyanate are particularly suitable. The preferred polyurethanes contain no significant amounts of reactive isocyanate groups and have good extensibility (elongation at break approximately from 400 to 700%) and a number-average molecular weight of approximately from 10,000 to 60,000. Their Shore A hardness is approximately from 60 to 100. The preferred polyurethanes are soluble in organic solvents, such as tetrahydrofuran, tetrahydrofuran-toluene mixtures, dioxane, cyclohexanone and dimethylformamide and some of them also in ketones, such as methyl ethyl ketone or acetone.

The conventional magnetic pigments can be used though the final properties of the magnetic coating also depend on the magnetic pigment used. Examples of the magnetic pigments are gamma-iron-(III) oxide, finely divided magnetite, ferromagnetic chromium dioxide, cobalt-modified γ-iron oxide and ferromagnetic metals and metal alloy pigments, such as alloys of iron, cobalt and nickel or of iron and cobalt (for example manufactured in accordance with German Pat. No. 1,247,026). The preferred magnetic pigment is acicular gamma-iron-(III) oxide. The particle size is in general from 0.2 to $2\mu$ and the range from 0.3 to $0.8\mu$ is preferred.

The ratio of magnetic pigment to binder in the recording media according to the invention is in general from 1 to 10 and especially from 2.5 to 5 parts by weight of magnetic pigment per part by weight of the binder mixture.

The non-magnetic and non-magnetizable base materials used are the conventional materials, in particular films of linear polyesters such as polyethylene terephthalate, in general in gauges of from 4 to $200\mu$ and especially of from 10 to $36\mu$.

The magnetic coatings can be produced by conventional methods. A suitable method is to prepare the magnetic dispersion from the magnetic pigment and a solution of the binder, dispersing agents, the lubricant and optionally other additives, in a dispersing apparatus, for example a tube mill or a stirred ball mill, to filter the dispersion and to apply it to the non-magnetizable base material using a conventional coating machine for example a knife coater. As a rule, the liquid coating mixture is subjected to magnetic orientation before it is dried on the base material; drying is suitably carried out for from 2 5 minutes at temperatures of from 50° to 90° C. The magnetic coatings can be smoothed and densified on conventional machinery by passing them between heated and polished rollers, if necessary using pressure and temperatures of from 50° to 100° C, preferably from 60° to 80° C. The thickness of the magnetic coating is in general from 3 to $20\mu$, preferably from 8 to $15\mu$.

The coated magnetic recording media according to the invention are distinguished by high abrasion resistance coupled with only little transfer of material to the magnetic heads, high stability under changing climatic conditions and non-cupping of the tapes under adverse climatic conditions, and at the same time have high sensitivity in recording and playback.

The parts and percentages mentioned in the examples which follow, and in the comparative experiment, are by weight, unless stated otherwise. Parts by volume bear the same relation to parts by weight as the liter to the kilogram.

EXPERIMENT A (COMPARATIVE EXPERIMENT)

8,000 Parts of 6 mm steel balls are introduced into a cylindrical steel mill of capacity 6,000 parts by volume and the following mixture is added: 700 parts of rod-shaped finely particulate gamma-iron-(III) oxide, 10.5 parts of soya lecithin, 4.2 parts of dioctyl azelate, 2.1 parts of polydimethylsiloxane, 250 parts of tetrahydrofuran, 250 parts of dioxane, 42 parts of carbon black and 1,360 parts of a 15% strength binder solution prepared by dissolving 192 parts of an elastomeric, thermoplastic polyester-urethane (prepared according to German Printed Application 1,106,959 from adipic acid, 1,4-butanediol and 4,4'-diisocyanatodiphenylmethane) and 48 parts of a commercially available high molecular weight epoxy resin, obtained from bisphenol A and epichlorohydrin and having an epoxide equivalent weight of approx. 10,000, in 1,360 parts of a mixture of equal parts of tetrahydrofuran and dioxane. The dispersing treatment is carried out for 92 hours and the dispersion is then filtered under pressure through a paper filter. The dispersion is used to coat a $36\mu$ polyethylene terephthalate film, the magnetic pigments being oriented by means of a permanent magnet. After drying, the resulting magnetic coating is $10\mu$ thick. The magnetic films are cut into ½ inch wide tapes, which are tested and give the following result:

| | |
|---|---|
| Coercive force (oersted) | 297 (23.6 kA/m) |
| Orientation ratio (Ratio of residual induction in the direction of tape travel to residual induction in the crosswise direction) | 1.7 |
| Electrical surface resistance of the magnetic coating (M ohm per square) | 69 |

COMPARATIVE EXPERIMENT B

A magnetic tape is produced exactly as described under Experiment A, but in addition to the materials mentioned, 8.5 parts of dicresyl-orthophosphphosphoric acid (an acid phosphorus compound according to German Printed Application No. 1,005,754) are charged into the steel mill. Tests of the tape, which in other respects was produced exactly as before, gave the following results

| | |
|---|---|
| Coercive force (oersted) | 299 (23.8 kA/m) |
| Orientation ratio | 1.50 |
| Electrical surface resistance (M ohm per square) | 25 |

COMPARATIVE EXPERIMENT C

A magnetic tape is produced as described under Experiment A, but in addition to the material mentioned, 35 parts of zinc-(II) laurylphosphonate according to German Published Application No. 1,669,602) are charged into the steel mill. Tests on the tape, which in other respects was produced exactly as before, gave the following result:

| Coercive force (oersted) | 296 (23.5 kA/m) |
|---|---|
| Orientation ratio | 1.55 |
| Electrical surface resistance (M ohm per square) | 55 |

EXAMPLE 1

A magnetic tape is produced exactly as described under Experiment A, but in addition to the materials mentioned, 4.8 parts of tri-n-butoxyethyl ester of phosphoric acid (of the above formula II) are charged into the steel mill. Tests on the tape, which in other respects was produced exactly as before, gave the following results:

| Coercive force (oersted) | 305 (24,3 kA/m) |
|---|---|
| Orientation ratio | 1.7 |
| Electrical surface resistance of the magnetic coating (M ohm per square) | 20 |

Comparative test of the tapes, produced according to Experiment A and according to Example 1, on a computer tape deck:

11 cm long pieces from each of the two types of tape were subjected to 50,000 reversals on an IBM 2401 computer tape deck. The increase in drop-out, the state of the signal level envelope, the tape surfaces and the condition of the magnetic head system were assessed.

For both types of tape, the drop-out rate and the signal level curves were approximately the same. The surface of the tape produced according to Experiment A showed clearly visible signs of wear, whilst the surface of the tape produced according to Example 1 appeared practically unchanged. When testing the tape from Experiment A, brown material deposited on the magnetic heads was detectable at the end of the test, but not in the case of the test of the tape from Example 1.

In the abovementioned comparative test on the computer tape deck, the drop-out rates of the as yet unused tapes B and C was about the same as that of the tapes produced according to Experiment A and Example 1. The signal level curve of the tape according to Comparative Experiment B was about 10% lower, for a recording density of 800 fci, than the signal level curve of the tape which had been produced according to Example 1, and the signal level curve of the tape according to Comparative Experiment C was approx. 5% lower than that of the tape according to Example 1. The tape surface produced according to comparative Experiment B showed distinct signs of wear after sustained operation and gave an increase in the number of drop-outs already after approx. 1,000 reversals. After completion of the test, distinct deposits of a brown powdery material abraded from the tape were visible on the write and read head.

The tape surface according to Comparative Experiment C also showed distinct traces of wear after sustained operation with this tape an increase in the drop-out rate occurring after about 15,000 reversals. After completion of the test, deposits of a smeary abraded material were present on the magnetic head.

EXAMPLE 2

The procedure followed is as in Example 1 but instead of the mixture of 4.2 parts of dioctyl azelate, 2.1 parts of polydimethylsiloxane and 4.8 parts of tri-n-butoxyethyl ester of phosphoric acid, 11.1 parts of the tri-n-butoxyethyl ester of phosphoric acid were employed. Tests on the tape, which in other respects was produced exactly as before, gave the following results:

| Coercive force (oersted) | 300 |
|---|---|
| Orientation ratio | 2.05 |
| Electrical surface resistance of the magnetic coating (M ohm per square) | 25 |

In a comparative test on a computer tape deck, carried out as indicated above, the drop-out rate and the signal level curve of the tape were approximately the same as for the tape produced according to Comparative Experiment A. The surface of the tape produced according to Example 2 was practically unchanged at the end of the experiment and there were no deposits on the magnetic head. The test was then repeated with the same piece of magnetic tape produced according to Example 2, and the same results were obtained.

We claim:

1. A coated magnetic recording medium comprising a base carrying a magnetic coating which consists essentially of a dispersion of a finely divided magnetic pigment and a lubricant in an organic binder, wherein the said lubricant contains 20 to 100% by weight of a compound of the formula (1)

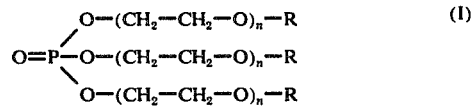

wherein $n$ is an integer of from 1 to 30 and R is alkyl, alkoxyalkyl or aralkyl, each of 3 to 18 carbon atoms.

2. A coated magnetic recording medium as claimed in claim 1, which contains a compound of the formula (I), in which each $n$ is 1 and each R is alkyl.

3. A magnetic recording medium as claimed in claim 2, wherein the lubricant present is a compound of the formula

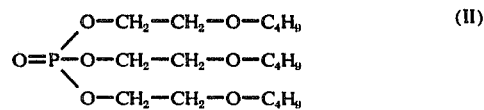

4. A magnetic recording medium as claimed in claim 1, which contains from 0.1 to 20 percent by weight of the lubricants, based on the amount of magnetic pigment.

5. A magnetic recording medium as claimed in claim 1, which contains from 0.4 to 2 percent by weight of the lubricants, based on the amount of magnetic pigment.

* * * * *